US010654729B2

(12) United States Patent
Mochizuki et al.

(10) Patent No.: US 10,654,729 B2
(45) Date of Patent: May 19, 2020

(54) FLUID STERILIZATION DEVICE

(71) Applicant: NIKKISO CO., LTD., Tokyo (JP)

(72) Inventors: Hiroaki Mochizuki, Hakusan (JP); Tetsumi Ochi, Tokyo (JP)

(73) Assignee: NIKKISO CO., LTD., Tokyo (JP)

( * ) Notice: Subject to any disclaimer, the term of this patent is extended or adjusted under 35 U.S.C. 154(b) by 0 days.

(21) Appl. No.: 16/404,310

(22) Filed: May 6, 2019

(65) Prior Publication Data
US 2019/0256381 A1 Aug. 22, 2019

Related U.S. Application Data

(63) Continuation of application No. PCT/JP2017/039745, filed on Nov. 2, 2017.

(30) Foreign Application Priority Data

Nov. 7, 2016 (JP) .................. 2006-217038

(51) Int. Cl.
*A61L 2/10* (2006.01)
*C02F 1/32* (2006.01)

(52) U.S. Cl.
CPC ................ *C02F 1/325* (2013.01); *A61L 2/10* (2013.01); *C02F 1/32* (2013.01); *A61L 2202/11* (2013.01); *C02F 2201/3222* (2013.01); *C02F 2209/03* (2013.01)

(58) Field of Classification Search
CPC .......... A61L 2/10; A61L 2202/11; C02F 1/32; C02F 1/325; C02F 2201/3222; C02F 2209/03
See application file for complete search history.

(56) References Cited

U.S. PATENT DOCUMENTS

| 3,566,105 A | * | 2/1971 | Wiltrout | A61L 2/10 |
| | | | | 250/373 |
| 10,280,093 B2 | * | 5/2019 | Takaoka | C02F 1/008 |
| 2008/0006832 A1 | * | 1/2008 | Haase | H01L 33/08 |
| | | | | 257/79 |

(Continued)

FOREIGN PATENT DOCUMENTS

| EP | 1310298 A1 | 5/2003 |
| JP | 2003-144913 A | 5/2003 |
| JP | 2014-233646 A | 12/2014 |

(Continued)

OTHER PUBLICATIONS

European Search Report dated Mar. 11, 2020 in EP Application No. 17867318.2.

*Primary Examiner* — Wyatt A Stoffa
(74) *Attorney, Agent, or Firm* — Muncy, Geissler, Olds & Lowe, PC

(57) ABSTRACT

A fluid sterilization device includes: a treatment flow passage in which a fluid subject to sterilization flows; a light source chamber that stores a light source for irradiating the fluid in the treatment flow passage with ultraviolet light; a window member that is provided between the treatment flow passage and the light source chamber and transmits ultraviolet light; and a pressure adjustment mechanism that adjusts a pressure in the light source chamber so as to reduce a difference between a pressure in the treatment flow passage and the pressure in the light source chamber.

8 Claims, 3 Drawing Sheets

(56) References Cited

U.S. PATENT DOCUMENTS

2008/0008632 A1* 1/2008 Engelhard ............... C01B 13/10
422/186.3
2015/0101968 A1* 4/2015 Yoon ....................... C02F 1/325
210/97

FOREIGN PATENT DOCUMENTS

JP 2014-233712 A 12/2014
WO WO 2016/008807 A1 1/2016

* cited by examiner

FLUID STERILIZATION DEVICE

RELATED APPLICATION

Priority is claimed to Japanese Patent Application No. 2016-217038, filed on Nov. 7, 2016, the entire content of which is incorporated herein by reference.

BACKGROUND OF THE INVENTION

1. Field of the Invention

The present invention relates to fluid sterilization devices and, more particularly, to a technology of sterilizing a fluid subject to treatment by irradiating the fluid with ultraviolet light.

2. Description of the Related Art

It is known that ultraviolet light has sterilization capability. Devices that radiate ultraviolet light are used for sterilization in medical and food processing fields. Devices that sterilize a fluid such as water continuously by irradiating the fluid with ultraviolet light are also used. One example of such a device is configured such that the ends of a straight pipe are sealed by quartz glass plates, and the fluid flowing in the pipe is irradiated with ultraviolet light from outside the pipe via the glass plates.

In a fluid sterilization device, it is required to employ a flow passage structure capable of withstanding the fluid pressure of the fluid that should be treated. In particular, it is required to configure the glass plate that provides a partition between the flow passage and the light source to have a pressure resisting structure. In the case the fluid subject to treatment has a high pressure, the thickness of the glass plate should be enlarged in order to withstand the pressure. If the thickness of the glass plate is enlarged, on the other hand, transmission through the thick glass plate increases a loss of ultraviolet light and lowers the intensity of ultraviolet light irradiating the fluid.

SUMMARY OF THE INVENTION

In this background, an illustrative purpose of the present invention is to provide a fluid sterilization device in which the efficiency of irradiating the fluid flowing in the flow passage with ultraviolet light is increased.

A fluid sterilization device according to an embodiment of the present invention includes: a treatment flow passage in which a fluid subject to sterilization flows; a light source chamber that stores a light source for irradiating the fluid in the treatment flow passage with ultraviolet light; a window member that is provided between the treatment flow passage and the light source chamber and transmits the ultraviolet light; and a pressure adjustment mechanism that adjusts a pressure in the light source chamber so as to reduce a difference between a pressure in the treatment flow passage and the pressure in the light source chamber.

According to the embodiment, the pressure in the light source chamber is adjusted in accordance with the pressure of the fluid in the treatment flow passage so that the pressure difference exerted on the respective faces of the window member is reduced. This allows employing a less thick window member than the case where the pressure in the light source chamber is not adjusted in accordance with the pressure in the treatment flow passage and a relatively large pressure difference is exerted on the window member as a result. The embodiment also increases the efficiency of irradiating the fluid with ultraviolet light.

The pressure adjustment mechanism may include a partition wall configured to be displaced in accordance with a pressure difference between the treatment flow passage and the light source chamber and adjust the pressure in the light source chamber by using volume change associated with displacement of the partition wall.

The pressure adjustment mechanism may include a light source side pressure adjustment chamber that communicates with the light source chamber and a flow passage side pressure adjustment chamber that communicates with the treatment flow passage, a partition wall being provided between the light source side pressure adjustment chamber and the flow passage side pressure adjustment chamber, and the pressure adjustment mechanism adjusting the pressure in the light source chamber by using volume change in the light source side pressure adjustment chamber associated with displacement of the partition wall.

The pressure adjustment mechanism may include a pressure adjustment chamber that communicates with the light source chamber, a partition wall being provided between the pressure adjustment chamber and the treatment flow passage, and the pressure adjustment mechanism adjusting the pressure in the light source chamber by using volume change in the pressure adjustment chamber associated with displacement of the partition wall.

The pressure adjustment chamber may be provided opposite to the light source chamber, sandwiching the treatment flow passage.

The partition wall may be provided between the treatment flow passage and the light source chamber, a portion of the partition wall being configured to be the window member, and the pressure adjustment mechanism may adjust the pressure in the light source chamber by using volume change in the light source chamber associated with displacement of the partition wall.

A gas of a pressure higher than the atmospheric pressure may be enclosed in the light source chamber.

The pressure adjustment mechanism may include an adjustable pressure device that pressurizes and depressurizes the light source chamber, a flow passage pressure gauge that measures the pressure in the treatment flow passage, and a control device that controls an operation of the adjustable pressure device based on a measurement result of the flow passage pressure gauge.

The adjustable pressure device may include a pump that pressurizes the light source chamber, a valve that depressurizes the light source chamber, and a light source chamber pressure gauge that measures the pressure in the light source chamber. The control device may activate the adjustable pressure device so as to reduce a difference in measurement results of the flow passage pressure gauge and the light source chamber pressure gauge.

The fluid sterilization device may include a control device that outputs an alert when a pressure difference between the treatment flow passage and the light source chamber exceeds a predetermined threshold value.

A fluid sterilization device according to another embodiment of the present invention includes: a treatment flow passage designed to cause a fluid subject to sterilization to flow in a predetermined operating pressure range; a light source chamber that stores a light source for irradiating the fluid in the treatment flow passage with ultraviolet light; and a window member that is provided between the treatment flow passage and the light source chamber and transmits the ultraviolet light. A gas of a pressure different from an ambient pressure at a place of installation of the treatment flow passage and between an intermediate value of an operating pressure range of the treatment flow passage and the ambient pressure is enclosed in the light source chamber.

According to the embodiment, the window member receives, while the fluid in a predetermined operating pressure range flows in the treatment flow passage, a fluid pressure from the side of the treatment flow passage and receives a pressure of a value between an intermediate value of the operating pressure range and the ambient pressure from the side of the light source chamber. Therefore, the pressure difference exerted on the respective faces of the window member is reduced as compared with the case where the interior of the light source chamber is at the ambient pressure. This allows employing a less thick window member than the case where the interior of the light source chamber in which the fluid is flowing is at the ambient pressure and increases the efficiency of irradiating the fluid with ultraviolet light.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

The invention will now be described by reference to the preferred embodiments. This does not intend to limit the scope of the present invention, but to exemplify the invention.

A detailed description will be given of embodiments of the present invention with reference to the drawings. Like numerals are used in the description to denote like elements and a duplicate description is omitted as appropriate.

First Embodiment

Figure 1:
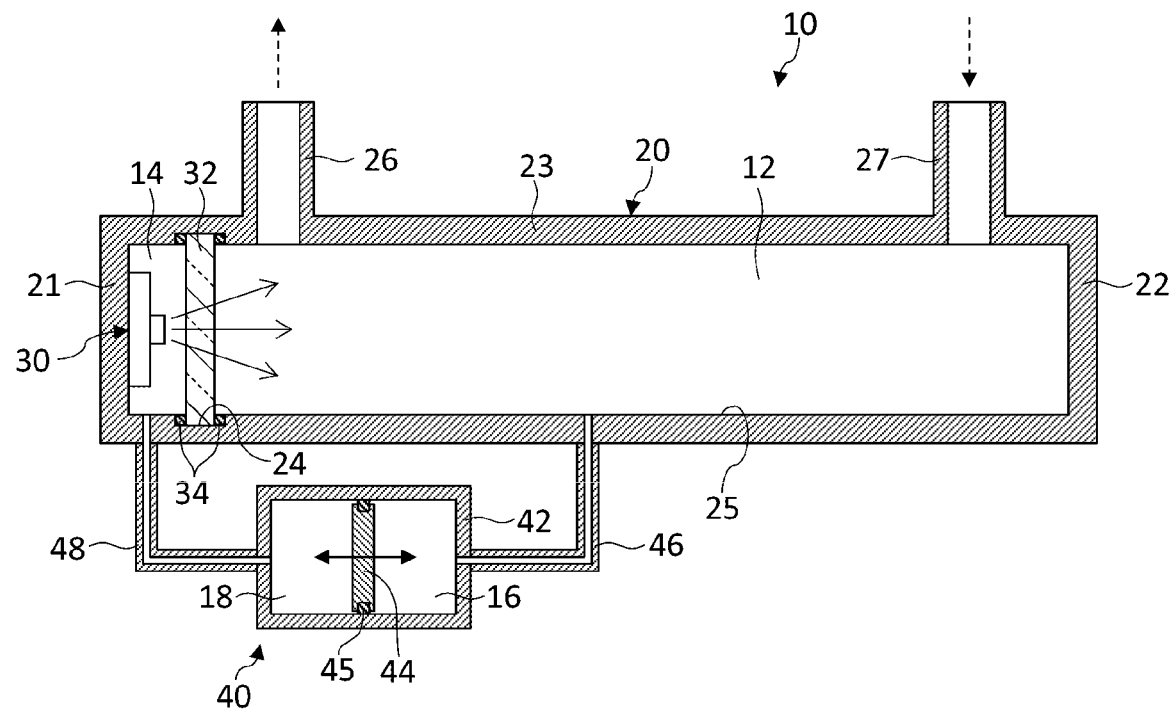
FIG. 1 is a cross-sectional view schematically showing a configuration of a fluid sterilization device according to the first embodiment.

FIG. 1 is a cross-sectional view schematically showing a configuration of a fluid sterilization device 10 according to the first embodiment. The fluid sterilization device 10 includes a treatment chamber 20, a light source 30, a window member 32, and a pressure adjustment mechanism 40. The light source 30 radiates ultraviolet light toward the interior of a treatment flow passage 12 bounded by the treatment chamber 20 and irradiates the fluid (water etc.) flowing in the treatment flow passage 12 with ultraviolet light so as to sterilize the fluid.

The treatment chamber 20 defines the treatment flow passage 12 and the light source chamber 14. The treatment chamber 20 includes a first end wall 21, a second end wall 22, a side wall 23, an outflow pipe 26, and an inflow pipe 27. A light source chamber 14 for accommodating the light source 30 is provided in the vicinity of the first end wall 21. The side wall 23 extends from the first end wall 21 toward the second end wall 22 in the axial direction. The side wall 23 is a tubular member and has, for example, a cylindrical shape. The side wall 23 is provided with the outflow pipe 26 and the inflow pipe 27. The outflow pipe 26 and the inflow pipe 27 communicate with the treatment flow passage 12. The outflow pipe 26 is provided in the vicinity of the window member 32, and the inflow pipe 27 is provided in the vicinity of the second end wall 22. An inner surface 25 of the treatment chamber 20 is made of an ultraviolet reflective material. For example, a fluororesin material like polytetrafluoroethylene (PTFE) or a metal material like aluminum (Al) is used.

The light source 30 is a so-called ultra violet-light emitting diode (UV-LED) light source that includes a light emitting device configured to emit ultraviolet light. It is preferred that the central wavelength or peak wavelength of the light emitting device included in the light source be included in a range of about 200 nm-350 nm and that the light emitting device emit ultraviolet light near 260 nm~290 nm having a high sterilizing efficiency. Such an ultraviolet LED is exemplified by an aluminum gallium nitride (AlGaN) based LED.

The light source 30 is provided in close proximity to the window member 32 and is arranged to irradiate the interior of the treatment flow passage 12 with ultraviolet light in the axial direction via the window member 32. The light source 30 may include an adjustment mechanism for adjusting the angle of light distribution of the light emitting device. In the case the directivity angle or orientation angle of the light emitting device included in the light source 30 is 60° or larger, 90° or larger, or 120° or larger, for example, the adjustment mechanism adjusts the output angle so that the angle of light distribution is 30° or smaller. The adjustment mechanism may be comprised of a transmission type optical system such as a lens or comprised of a reflection type optical system such as a concave mirror.

The window member 32 is provided to provide a partition between the treatment flow passage 12 and the light source chamber 14. For example, the window member 32 is laid in a recess 24 formed in the side wall 23 of the treatment chamber 20. A seal member 34 is provided in a gap between the window member 32 and the recess 24. This seals or encapsulates the light source chamber 14 against the fluid flowing in the treatment flow passage 12. The window member 32 is made of a material having a high ultraviolet transmittance such as quartz ($SiO_2$), sapphire ($Al_2O_3$), and amorphous fluororesin.

The pressure adjustment mechanism 40 includes a pressure adjustment chamber 42, a partition wall 44, a flow passage connection pipe 46, and a light source chamber connection pipe 48. The pressure adjustment mechanism 40 is provided to reduce a pressure difference exerted on the respective faces of the window member 32 and prevent damage to the window member 32 from the fluid pressure in the treatment flow passage 12.

The pressure adjustment chamber 42 is a chamber provided separately from the treatment chamber 20. The partition wall 44 is provided in the pressure adjustment chamber 42 and partitions the interior of the pressure adjustment chamber 42 into a flow passage side pressure adjustment chamber 16 and a light source side pressure adjustment chamber 18. The partition wall 44 is attached to the inner surface of the pressure adjustment chamber 42 via a slide member 45 and is configured to be slidable in a direction (the direction of the arrow in the figure) in which the flow passage side pressure adjustment chamber 16 and the light source side pressure adjustment chamber 18 are adjacent. The slide member 45 is configured such that the partition wall 44 is slidable while the space between the flow passage side pressure adjustment chamber 16 and the light source side pressure adjustment chamber 18 remains sealed or encapsulated by the partition wall 44. For example, the slide member 45 is formed by a seal member for piston seal.

The flow passage connection pipe 46 is a pipe that connects the treatment flow passage 12 and the flow passage side pressure adjustment chamber 16. The flow passage connection pipe 46 provides communication between the treatment flow passage 12 and the flow passage side pressure adjustment chamber 16 and ensures that the treatment flow passage 12 and the flow passage side pressure adjustment chamber 16 are at the same pressure inside. The light source chamber connection pipe 48 is a pipe that connects the light source chamber 14 and the light source side pressure adjustment chamber 18. The light source chamber connection pipe 48 provides communication between the light source chamber 14 and the light source side pressure adjustment chamber 18 and ensures that light source chamber 14 and the light source side pressure adjustment chamber 18 are at the same pressure.

The light source chamber 14 and the light source side pressure adjustment chamber 18 form a space sealed by the window member 32, the seal member 34, the partition wall 44, and the slide member 45. A gas such as air and nitrogen (N2) is enclosed in the light source chamber 14 and the light source side pressure adjustment chamber 18. The light source chamber 14 may be provided with a sensor for sensing leakage of the fluid from the treatment flow passage 12. The leakage sensing sensor provided in the light source chamber 14 is configured to output an alert when the leakage of the fluid is sensed.

The partition wall 44 is displaced by making a slide movement in accordance with a pressure difference between the flow passage side pressure adjustment chamber 16 and the light source side pressure adjustment chamber 18, i.e., a pressure difference between the treatment flow passage 12 and the light source chamber 14. When the partition wall 44 is displaced, the volume of the light source side pressure adjustment chamber 18 changes. In association with the volume change, the gas pressure in the light source chamber 14 and the light source side pressure adjustment chamber 18 changes. When the partition wall 44 is displaced such that the volume of the light source side pressure adjustment chamber 18 is reduced, the gas in the light source side pressure adjustment chamber 18 is compressed and the pressure is increased. When the partition wall 44 is displaced such that the volume of the light source side pressure adjustment chamber 18 is enlarged, on the other hand, the gas pressure in the light source side pressure adjustment chamber 18 is reduced. Thus, the partition wall 44 is displaced to reduce a pressure difference between the flow passage side pressure adjustment chamber 16 and the light source side pressure adjustment chamber 18 and adjusts the pressure in the light source chamber 14 such that the pressure difference between the treatment flow passage 12 and the light source chamber 14 is reduced.

The pressure adjustment mechanism 40 is configured to be capable of adjusting the pressure in a range between the first pressure and the second pressure. The first pressure corresponds to the gas pressure in the light source chamber 14 and the light source side pressure adjustment chamber 18 occurring when the volume of the light source side pressure adjustment chamber 18 is maximized. The second pressure corresponds to the gas pressure in the light source chamber 14 and the light source side pressure adjustment chamber 18 occurring when the volume of the light source side pressure adjustment chamber 18 is minimized. The value of the first pressure is not limited to any particular value, but it is preferred that the value is approximate to the atmospheric pressure (about 0.1 MPa). By making the first pressure value approximate to the atmospheric pressure, the pressure difference between the treatment flow passage 12 and the light source chamber 14 is minimized while the fluid sterilization device 10 is not being used. In the case the environment in which the fluid sterilization device 10 is installed is at a predetermined ambient pressure different from the atmospheric pressure, the first pressure may be approximate to the ambient pressure.

Meanwhile, the value of the second pressure is determined in accordance with the fluid pressure of the fluid subject to treatment. For example, a value about twice~ten times the atmospheric pressure (about 0.2 MPa~10 MPa) is set. Setting the second pressure value to be equal to or higher than the upper limit pressure of the fluid subject to treatment makes the pressure difference between the treatment flow passage 12 and the light source chamber 14 as small as possible and ensures a substantially zero pressure. The second pressure value may be less than the upper limit pressure of the fluid subject to treatment. This is because, even if the pressure in the light source chamber 14 can only be adjusted to a pressure lower than the pressure in the treatment flow passage 12 while the fluid sterilization device 10 is being used, the pressure difference between the treatment flow passage 12 and the light source chamber 14 is mitigated as compared with the case where the light source chamber 14 is at the atmospheric pressure.

A description will now be given of the operation of the fluid sterilization device 10 configured as described above. When the fluid is introduced into the interior of the treatment flow passage 12 while the fluid sterilization device 10 is being used, the pressure in the flow passage side pressure adjustment chamber 16 is increased in accordance with the fluid pressure in the treatment flow passage 12, and the partition wall 44 is displaced to mitigate the pressure difference between the flow passage side pressure adjustment chamber 16 and the light source side pressure adjustment chamber 18. As a result, the pressure in the light source chamber 14 is increased in association with the increase in the fluid pressure in the treatment flow passage 12, causing the pressure in the light source chamber 14 to be the fluid pressure or the second pressure value. The light source 30 irradiates the fluid flowing in the treatment flow passage 12 via the window member 32 to sterilize the fluid.

When the flow of the fluid in the treatment flow passage 12 is stopped and the fluid pressure is lowered, the pressure in the flow passage side pressure adjustment chamber 16 is lowered, and the partition wall 44 is displaced to mitigate the pressure difference between the flow passage side pressure adjustment chamber 16 and the light source side pressure adjustment chamber 18. As a result, the pressure in the light source chamber 14 is lowered in association with the lowering of the fluid pressure in the treatment flow passage 12. When the fluid sterilization device 10 is no longer used and the treatment flow passage 12 becomes empty and placed in the atmospheric pressure, the pressure in the light source chamber 14 becomes the atmospheric pressure or the first pressure value. Thus, the pressure adjustment mechanism 40 operates to mitigate the pressure difference between the treatment flow passage 12 and the light source chamber 14 both while the fluid sterilization device 10 is being used and while it is not being used.

According to the embodiment, the pressure adjustment mechanism 40 mitigates the pressure difference between the treatment flow passage 12 and the light source chamber 14 while the fluid sterilization device 10 is being used or while it is not being used. Accordingly, the force exerted on the window member 32 due to the pressure difference is always controlled to be small. This eliminates the need to increase the thickness of the window member 32 to withstand the pressure of the fluid flowing in the treatment flow passage 12 and makes it possible to make the window member 32 thin even when a high-pressure fluid is treated. The thin window member 32 inhibits a loss of ultraviolet light transmitted through the window member 32 and increase the intensity of ultraviolet light irradiating the fluid flowing in the treatment flow passage 12. The thin window member 32 also helps lower the cost of the window member 32 and the seal member 34.

In this embodiment, the case where the operating pressure range of the fluid is higher than the atmospheric pressure or the ambient pressure is shown. In one variation, the atmospheric pressure or the ambient pressure may be included in the operating pressure range, or the operating pressure range may be lower than the atmospheric pressure or the ambient pressure. Even in these cases, the maximum value of the pressure difference exerted on the window member 32 is reduced to allow a thinner window member 32 to be employed than in the case where pressure adjustment is not made, by activating the pressure adjustment mechanism 40 to reduce the pressure difference between the treatment flow passage 12 and the light source chamber 14.

(Variation 1)

Figure 2:
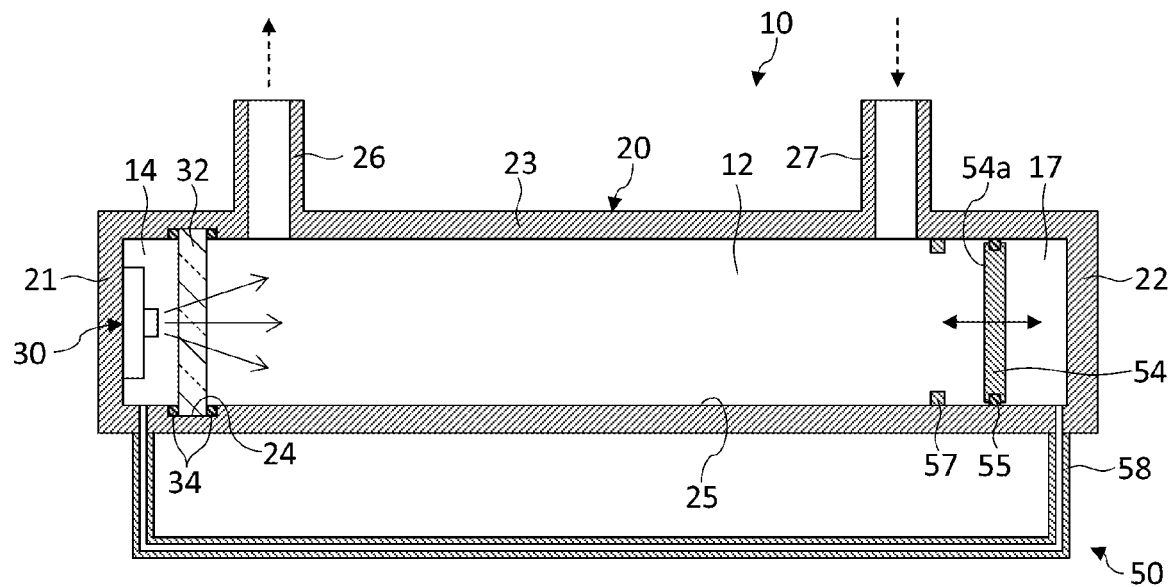
FIG. 2 is a cross-sectional view schematically showing a configuration of the fluid sterilization device according to a variation.

FIG. 2 is a cross-sectional view schematically showing a configuration of the fluid sterilization device 10 according to variation 1. The fluid sterilization device 10 according to the variation is provided with an alternative pressure adjustment mechanism 50 instead of the pressure adjustment mechanism 40. The pressure adjustment mechanism 50 is configured to adjust the pressure in the light source chamber 14 by using a pressure adjustment chamber 17 defined in the treatment chamber 20. The following description of the variation highlights the difference from the embodiment described above.

The pressure adjustment mechanism 50 includes a partition wall 54 and a connection pipe 58. The partition wall 54 is provided to provide a partition between the treatment flow passage 12 and the pressure adjustment chamber 17 in the treatment chamber 20. Accordingly, the pressure adjustment chamber 17 is defined by the second end wall 22, the side wall 23, and the partition wall 54 and is provided at a position opposite to the light source chamber 14, sandwiching the treatment flow passage 12.

The partition wall 54 is attached to the inner surface 25 of the treatment chamber 20 via a slide member 55. The partition wall 54 is provided in the vicinity of the second end wall 22 and is configured to be slidable between the second end wall 22 and the inflow pipe 27 in the axial direction of the treatment chamber 20 (the direction of the arrow in the figure). A stopper 57 is provided on the inner surface 25 in the vicinity of the inflow pipe 27. The stopper 57 restricts the displacement of the partition wall 54 to prevent the partition wall 54 from moving in a direction away from the second end wall 22 beyond the position of the inflow pipe 27. The partition wall 54 may be made of a material having a high ultraviolet reflectivity. For example, an opposing surface 54a of the partition wall 54 facing the light source 30 may be made of a material having a high ultraviolet reflectivity.

The connection pipe 58 connects the light source chamber 14 and the pressure adjustment chamber 17 and ensures that the light source chamber 14 and the pressure adjustment chamber 17 are at the same pressure. The connection pipe 58 extends along the side wall 23 of the treatment chamber 20 in the axial direction and connects the light source chamber 14 provided at the first end wall 21 and the pressure adjustment chamber 17 provided at the second end wall 22. As illustrated, the connection pipe 58 is provided outside the treatment chamber 20. The connection pipe 58 may be integrated with the treatment chamber 20. For example, the connection pipe 58 may be embedded in the side wall 23 of the treatment chamber 20.

According to the variation, the partition wall 54 is displaced in accordance with the pressure difference between the treatment flow passage 12 and the pressure adjustment chamber 17 to change the volume of the pressure adjustment chamber 17. Thereby, the pressure in the light source chamber 14 and the pressure adjustment chamber 17 is adjusted. Therefore, this variation is equally capable of adjusting the pressure in the light source chamber 14 to reduce the pressure difference between the treatment flow passage 12 and the light source chamber 14 both while the fluid sterilization device 10 is being used and while it is not being used.

(Variation 2)

Figure 3:
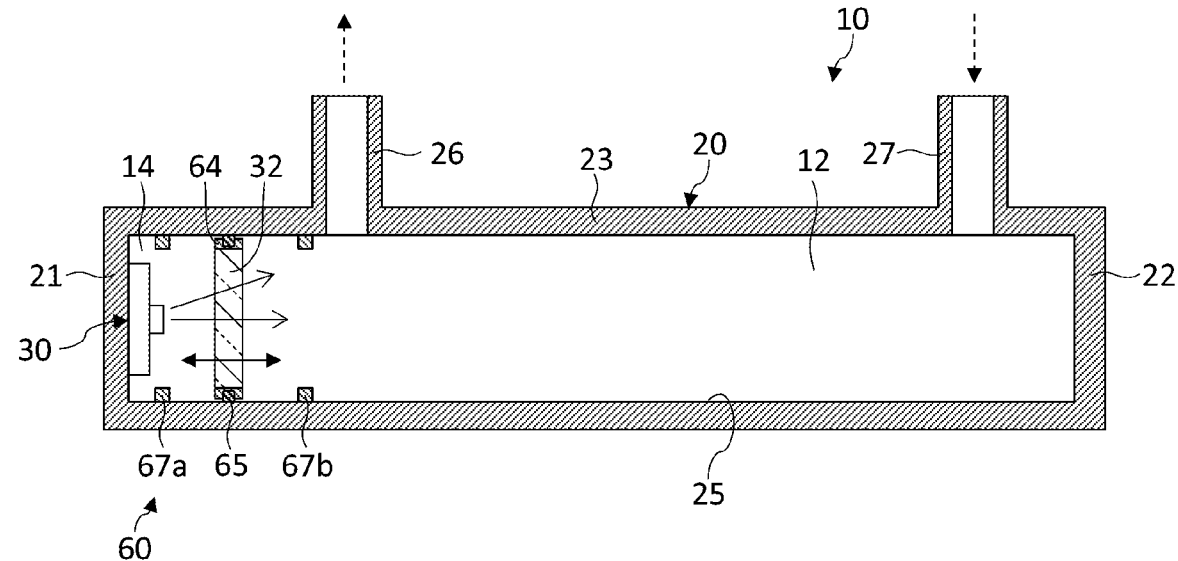
FIG. 3 is a cross-sectional view schematically showing a configuration of the fluid sterilization device according to a variation.

FIG. 3 is a cross-sectional view schematically showing a configuration of the fluid sterilization device 10 according to variation 2. The fluid sterilization device 10 according to the variation is provided with a pressure adjustment mechanism 60 instead of the pressure adjustment mechanism 40. The pressure adjustment mechanism 60 allows the light source chamber 14 to function as a pressure adjustment chamber by configuring the window member 32 to be movable. The following description of the variation highlights the difference from the embodiment described above.

The pressure adjustment mechanism 60 is provided with a partition wall 64. The partition wall 64 is provided to provide a partition between the treatment flow passage 12 and the light source chamber 14 in the treatment chamber 20. The partition wall 64 is provided with the window member 32, and at least a portion of the partition wall 64 is made of a material that transmits ultraviolet light. The partition wall 64 is attached to the inner surface 25 of the treatment chamber 20 via a slide member 65 and is configured to be slidable between the light source 30 and the outflow pipe 26 in the axial direction of the treatment chamber 20 (the direction of the arrow in the figure). A first stopper 67a is provided in the vicinity of the light source 30, and the partition wall 64 is preventing by the first stopper 67a from coming into contact with the light source 30. Further, a second stopper 67b is provided in the vicinity of the outflow pipe 26, and the displacement of the partition wall 64 is restricted to prevent the partition wall 64 from moving in a direction away from the first end wall 21 beyond the position of the outflow pipe 26.

According to this variation, the partition wall 64 that also serves as the window member 32 is displaced so as to change the volume of the light source chamber 14 and adjust the pressure in the light source chamber 14. Therefore, the variation is equally capable of adjusting the pressure in the light source chamber 14 to reduce the pressure difference between the treatment flow passage 12 and the light source chamber 14 both while the fluid sterilization device 10 is being used and while it is not being used.

(Variation 3)

In the embodiment and the variations described above, configurations are shown in which the volume of the pressure adjustment chamber is changed by causing the partition wall to make a slide movement. In a further variation, the device may be configured to make the volume of the pressure adjustment chamber variable by means of an alternative structure. For example, the device may be configured to make the volume of the pressure adjustment chamber variable by forming the partition wall with a flexible material and allowing the partition wall to be deformed. For example, a diaphragm structure may be used in the partition wall so that the volume of the pressure adjustment chamber is changed according to the deformation of the diaphragm. In other words, the device may be configured such that the partition wall is deformed to displace at least a portion of the partition wall, and the volume of the pressure adjustment chamber is changed accordingly.

Second Embodiment

Figure 4:
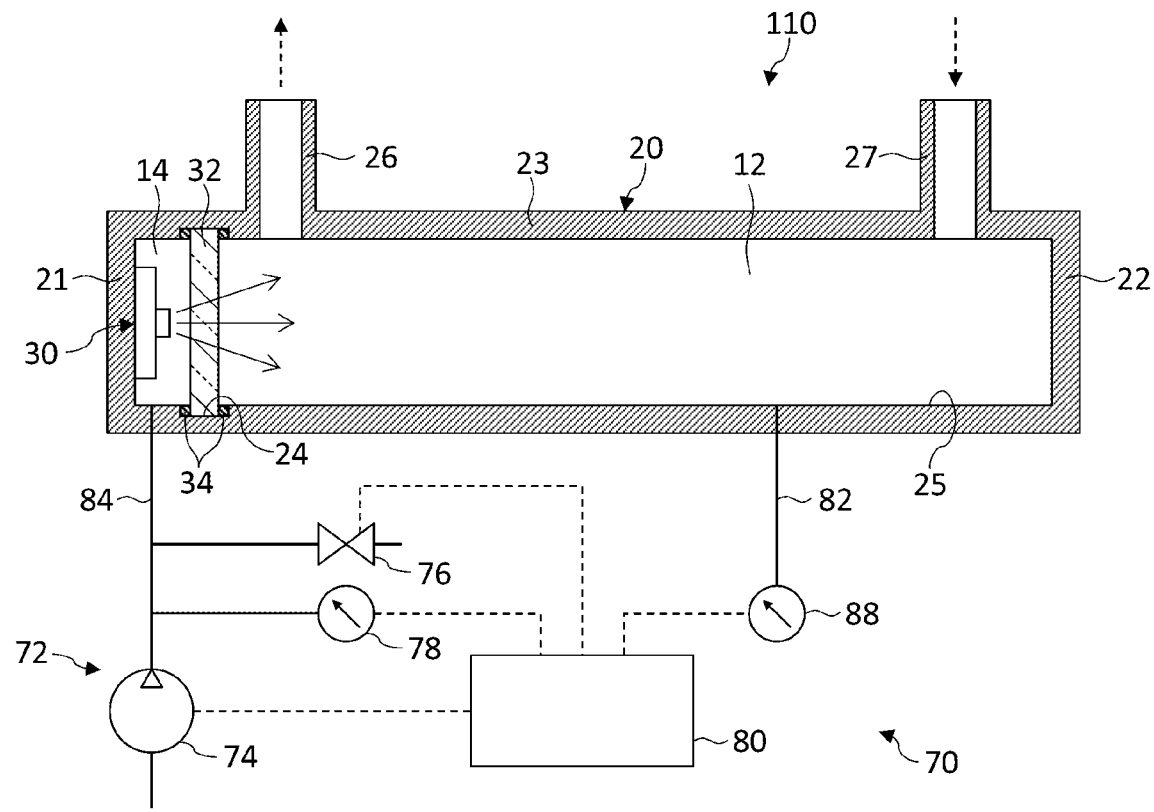
FIG. 4 is a cross-sectional view schematically showing a configuration of a fluid sterilization device according to the second embodiment.

FIG. 4 is a cross-sectional view schematically showing a configuration of a fluid sterilization device 110 according to the second embodiment. The fluid sterilization device 110 is provided with the treatment chamber 20, the light source 30, the window member 32, and a pressure adjustment mechanism 70. The pressure adjustment mechanism 70 includes an adjustable pressure device 72, a control device 80, and a flow passage pressure gauge 88. In this embodiment, the pressure in the light source chamber 14 is adjusted by activating the adjustable pressure device 72 in accordance with the pressure value of the treatment flow passage 12. A description will now be given of the fluid sterilization device 110, highlighting a difference from the embodiments described above.

The adjustable pressure device 72 includes a pressurizing pump 74, a depressurizing valve 76, and a light source chamber pressure gauge 78. The adjustable pressure device 72 is connected to a light source chamber connection pipe 84 that communicates with the light source chamber 14. The pressurizing pump 74 is configured to supply pressurized air or nitrogen gas to the light source chamber 14 via the light source chamber connection pipe 84 and pressurize the light source chamber 14. The depressurizing valve 76 is configured to lower the pressure in the light source chamber 14 by venting the pressurized light source chamber 14. The light source chamber pressure gauge 78 measures the pressure in the light source chamber 14. The flow passage pressure gauge 88 is connected to the treatment flow passage 12 via the flow passage connection pipe 82 and measures the fluid pressure in the treatment flow passage 12. The pressurizing pump 74, the depressurizing valve 76, the light source chamber pressure gauge 78, and the flow passage pressure gauge 88 are connected to the control device 80 and are activated in accordance with a command from the control device 80.

The control device 80 controls the operation of the adjustable pressure device 72 in accordance with the pressure value of the treatment flow passage 12 measured by the flow passage pressure gauge 88. In the event that the pressure value of the treatment flow passage 12 increases, the control device 80 pressurizes the light source chamber 14 by activating the pressurizing pump 74, thereby reducing the pressure difference between the treatment flow passage 12 and the light source chamber 14. In the vent that the pressure value of the treatment flow passage 12 decreases, the control device 80 depressurizes the light source chamber 14 by activating the depressurizing valve 76, thereby reducing the pressure difference between the treatment flow passage 12 and the light source chamber 14. For example, the control device 80 subjects the pressurizing pump 74 and the depressurizing valve 76 to feedback control in such a manner as to reduce the difference between the pressure value of the light source chamber pressure gauge 78 and the pressure value of the flow passage pressure gauge 88.

The control device 80 may output an alert indicating abnormality when the adjustable pressure device 72 does not operate normally. For example, the control device 80 outputs an alert when the pressure difference between the treatment flow passage 12 and the light source chamber 14 exceeds a predetermined threshold value. This may alert the user of the likelihood of damage to the window member 32 or impairing of the sealing by the seal member 34.

According to the embodiment, the pressure in the light source chamber 14 is adjusted by activating the adjustable pressure device 72 in accordance with the pressure value of the flow passage pressure gauge 88. Therefore, according to the embodiment, the pressure in the light source chamber 14 is adjusted to reduce the pressure difference between the treatment flow passage 12 and the light source chamber 14 even when the fluid pressure in the treatment flow passage 12 is high.

Third Embodiment

Figure 5:
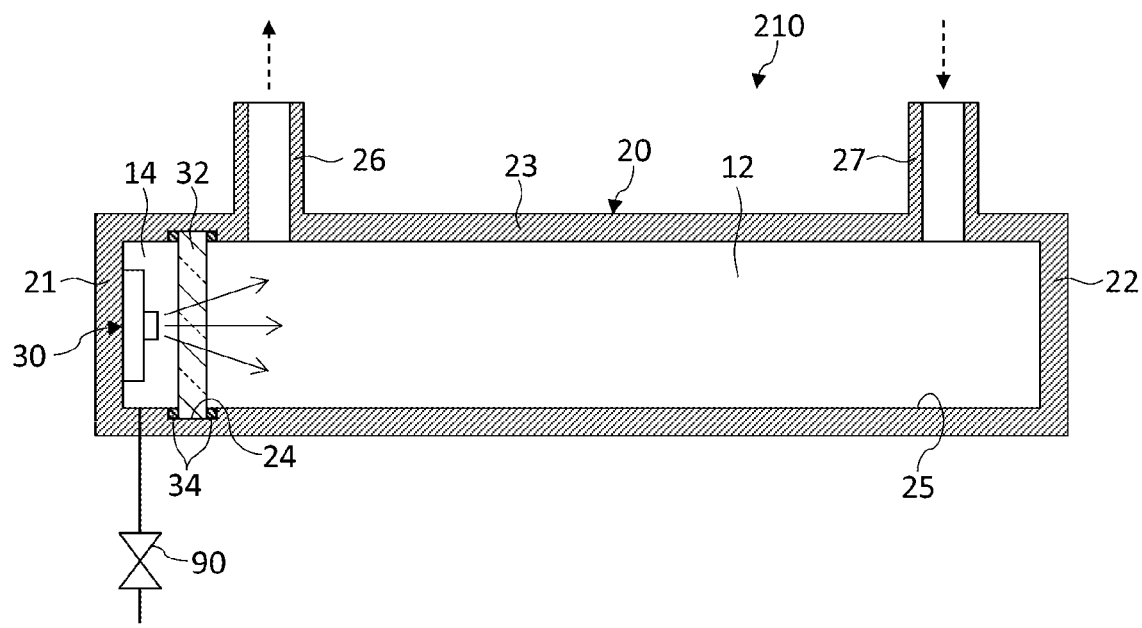
FIG. 5 is a cross-sectional view schematically showing a configuration of a fluid sterilization device according to the third embodiment.

FIG. 5 is a cross-sectional view schematically showing a configuration of a fluid sterilization device 210 according to the third embodiment. The fluid sterilization device 210 is provided with the treatment chamber 20, the light source 30, the window member 32, and a valve 90. In this embodiment, the pressure adjustment mechanism as shown in the embodiments and variations described above is not provided, and the pressure in the light source chamber 14 is maintained at a constant value. The valve 90 is connected to the light source chamber 14, and a gas at a predetermined pressure is enclosed in the light source chamber 14. In this embodiment, the maximum value of the pressure difference exerted on the window member 32 is mitigated by enclosing a gas at a predetermined pressure in the light source chamber 14.

The pressure value of the gas enclosed in the light source chamber 14 is a value between an intermediate value of the operating pressure range of the fluid flowing in the treatment flow passage 12 and the ambient pressure of the place of installation of the treatment flow passage 12. For example, given that the operating pressure range of the fluid flowing in the treatment flow passage 12 is 0.3 MPa~0.5 MPa, and the ambient pressure of the place of installation of the treatment flow passage 12 is the atmospheric pressure (about 0.1 MPa), a gas between 0.1 MPa~0.4 MPa is enclosed in the light source chamber 14. It is preferred that the pressure value of the light source chamber 14 be set such that the maximum value of the pressure difference exerted on the window member 32 is small. For example, the pressure is set to a value near the intermediate value between the upper or lower limit (marginal value) of the operating pressure range of the treatment flow passage 12 and the ambient pressure. For example, the pressure value of the light source chamber 14 may be set to a value about 0.5~1.5 times the intermediate value between the marginal value of the operating pressure range of the treatment flow passage 12 and the ambient pressure.

The ambient pressure of the treatment flow passage 12 may be equal to the atmospheric pressure, lower than the atmospheric pressure, or higher than the atmospheric pressure. Further, the operating pressure range of the fluid flowing in the treatment flow passage 12 may include the ambient pressure of the place of installation of the treatment flow passage 12. In the case the operating pressure range of the treatment flow passage 12 is lower than the ambient pressure, for example, the pressure in the light source chamber 14 may be lower than the ambient pressure. The pressure value of the light source chamber 14 may be different from or equal to the value of the ambient pressure.

According to the embodiment, the light source chamber 14 is set to a predetermined pressure and is at a pressure between the operating pressure range of the fluid flowing in the treatment flow passage 12 and the ambient pressure. Therefore, the maximum value of the pressure difference exerted on the respective faces of the window member 32 is reduced. For example, given that the operating pressure range of the fluid is 0.3 MPa~0.5 MPa, and the pressure in the light source chamber 14 is 0.3 MPa, the pressure difference exerted on the window member 32 while the fluid flows in the treatment flow passage 12 is 0.2 MPa at a maximum. Even when the treatment flow passage 12 becomes empty and placed in the ambient pressure (e.g., the atmospheric pressure of about 0.1 MPa), the pressure difference exerted on the window member 32 will be about 0.2 MPa. As a result, the maximum value of the pressure exerted on the respective faces of the window member 32 is ensured to be smaller than the upper limit value of the fluid pressure. This makes the maximum value of the force exerted on the window member 32 due to the pressure difference smaller as compared with the case where the light source chamber 14 is not set to a predetermined pressure. Thus, this embodiment makes it possible to use the window member 32 of a small thickness for treatment of the fluid for which the difference between the operating pressure range of the fluid and the ambient pressure is large.

Described above is an explanation based on an exemplary embodiment. The embodiment is intended to be illustrative only and it will be understood by those skilled in the art that various design changes are possible and various modifications are possible and that such modifications are also within the scope of the present invention.

The device according to the embodiments and variations is described as a device for irradiating the fluid with ultraviolet light so as to sterilize the fluid. In one variation, the inventive sterilization device may be used for a purification process that decomposes organic substance included in a fluid by using ultraviolet irradiation.

In a still further variation, the fluid may be caused to flow in a direction opposite to the direction of flow illustrated in the embodiments or variations described above. In other words, the inflow port and the outflow port may be used the other way around. For example, the communication port denoted by the reference numeral 27 may be used as the outflow port and the communication port denoted by the reference numeral 26 may be used as the inflow port in the first embodiment shown in FIG. 1.

It should be understood that the invention is not limited to the above-described embodiment but may be modified into various forms on the basis of the spirit of the invention. Additionally, the modifications are included in the scope of the invention.

What is claimed is:

1. A fluid sterilization device comprising:
    a treatment flow passage in which a fluid subject to sterilization flows;
    a light source chamber that stores a light source for irradiating the fluid in the treatment flow passage with ultraviolet light;
    a window member that is provided between the treatment flow passage and the light source chamber and transmits the ultraviolet light; and
    a pressure adjustment mechanism that includes a partition wall configured to be displaced in accordance with a pressure difference between the treatment flow passage and the light source chamber and adjusts a pressure in the light source chamber by using volume change associated with a displacement of the partition wall so as to reduce the pressure difference between the treatment flow passage and the light source chamber.

2. The fluid sterilization device according to claim 1, wherein
    the partition wall is configured to be slidable so as to reduce the pressure difference between the light source chamber and the treatment flow passage.

3. The fluid sterilization device according to claim 1, wherein
    at least a portion of the partition wall is made of a flexible material, and the partition wall is configured to be displaced so as to reduce the pressure difference between the light source chamber and the treatment flow passage.

4. The fluid sterilization device according to claim 1, wherein
    the pressure adjustment mechanism includes a light source side pressure adjustment chamber that communicates with the light source chamber and a flow passage side pressure adjustment chamber that communicates with the treatment flow passage, the partition wall is provided between the light source side pressure adjustment chamber and the flow passage side pressure adjustment chamber, and the pressure adjustment mechanism adjusts the pressure in the light source chamber by using a volume change in the light source side pressure adjustment chamber associated with the displacement of the partition wall.

5. The fluid sterilization device according to claim 1, wherein
    the pressure adjustment mechanism includes a pressure adjustment chamber that communicates with the light source chamber, the partition wall is provided between the pressure adjustment chamber and the treatment flow passage, and the pressure adjustment mechanism adjusts the pressure in the light source chamber by using a volume change in the pressure adjustment chamber associated with the displacement of the partition wall.

6. The fluid sterilization device according to claim 5, wherein
    the pressure adjustment chamber is provided opposite to the light source chamber, sandwiching the treatment flow passage.

7. The fluid sterilization device according to claim 1, wherein
    the partition wall is provided between the treatment flow passage and the light source chamber, a portion of the partition wall is configured to be the window member, and the pressure adjustment mechanism adjusts the pressure in the light source chamber by using a volume change in the light source chamber associated with the displacement of the partition wall.

8. The fluid sterilization device according to claim 1 comprising a control device that outputs an alert when the pressure difference between the treatment flow passage and the light source chamber exceeds a predetermined threshold value.

* * * * *

UNITED STATES PATENT AND TRADEMARK OFFICE
CERTIFICATE OF CORRECTION

Page 1 of 1

PATENT NO.          : 10,654,729 B2
APPLICATION NO.     : 16/404310
DATED               : May 19, 2020
INVENTOR(S)         : Hiroaki Mochizuki and Tetsumi Ochi It is certified that error appears in the above-identified patent and that said Letters Patent is hereby corrected as shown below:

On the Title Page

(30) Foreign Application Priority Data reads:
"Nov. 7, 2016 (JP) .............................. 2006-217038"
Should read:
-- Nov. 7, 2016 (JP) .............................. 2016-217038 --

Signed and Sealed this
Twenty-second Day of December, 2020

Andrei Iancu
*Director of the United States Patent and Trademark Office*